United States Patent [19]

Pozzi

[11] Patent Number: 5,066,227
[45] Date of Patent: Nov. 19, 1991

[54] DENTAL TOOTH SHADE MATCHING SYSTEM

[76] Inventor: Bruno Pozzi, 425 Deseo Ave., Camarillo, Calif. 93010

[21] Appl. No.: 686,809
[22] Filed: Apr. 17, 1991
[51] Int. Cl.⁵ .............................................. A61C 19/10
[52] U.S. Cl. ........................................................ 433/26
[58] Field of Search .......................................... 433/26

[56] References Cited

U.S. PATENT DOCUMENTS 4,115,922  9/1978  Alderman ............................. 433/26
4,541,801  9/1985  Mackert et al. ...................... 433/26

Primary Examiner—John J. Wilson
Attorney, Agent, or Firm—Bauer & Schaffer

[57] ABSTRACT

A system for selecting a tooth color for a patient for whom artificial teeth are to be made which is provided with a holder having a plurality of slots and identical dual shade guides. The shade guides are removably supported in the slots and include areas on the surface for recording a patient's identifying data and the tooth data. When in use, one of the guides is removed from the holder and sent to the technician for use in making the teeth for the patient, while the other of the guides is retained by the dentist.

4 Claims, 1 Drawing Sheet

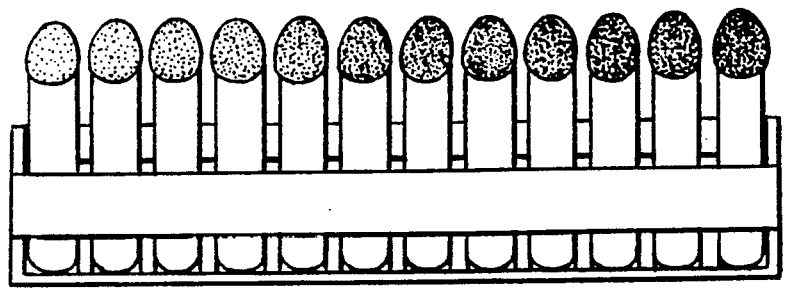
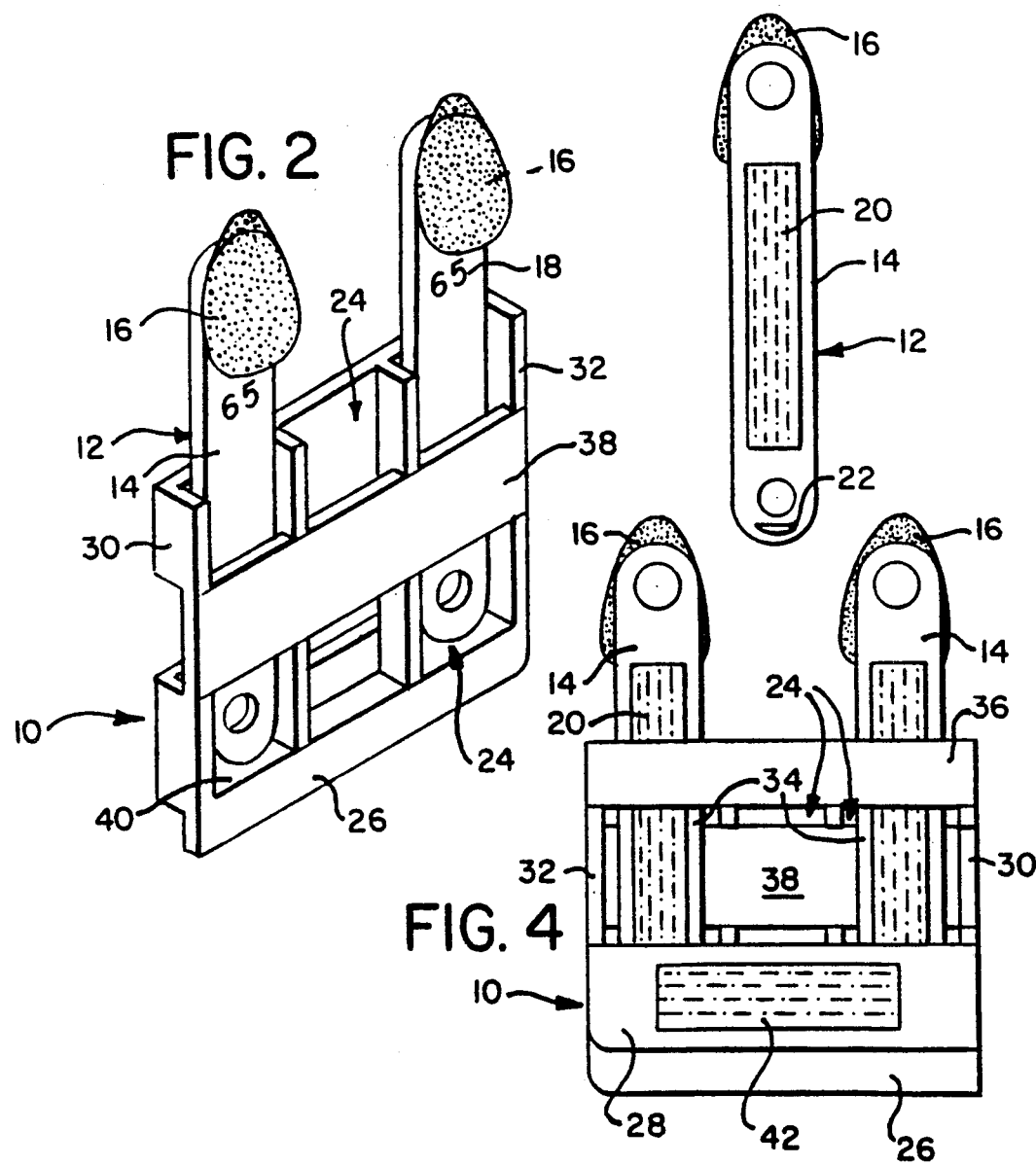

DENTAL TOOTH SHADE MATCHING SYSTEM

BACKGROUND OF THE INVENTION

The present invention relates to a system for facilitating and improving the procedure for selecting the proper color for artificial teeth in the creation of lifelike teeth replacement and bridgework.

The creation of false teeth and bridges is no longer a major engineering or physical task for the dentist, prosthodontist or even the technician, (hereinafter simply referred to as the dentist) since the advent of plastic teeth and bridge supports have allowed the almost precise reconstruction of the gum and teeth configurations. On the other hand, a considerable proportion of the time and cost for reconstructing a patient's mouth is spent on the aesthetics involved therein, and in particular, in determining the proper color, shade, and other characteristics of the artificial teeth in order that the new teeth match closely with the original as well as to provide a most natural appearance for the wearer.

A dentist must initially prepare the patient's mouth, in order to fabricate dental appliances, (commonly called dentures), such as partials, crowns, bridges, veneers, laminates, over dentures, implants (an implant to be finished needs the reconstruction of false teeth and supporting structure). After the preparation has been done, an impression is usually obtained. At this point, it is necessary for the dentist to decide on the shade/color of any replacement of the teeth. This procedure is normally done by using a shade guide such as that shown in FIG. 1. Shade guides are made by manufacturers of prefabricated teeth for use as dentures, partials and implant over dentures. Crowns, bridges, laminates and veneers are, on the other hand, generally manufactured by dental laboratories using tooth powder materials (resins or porcelain) which have also been manufactured by tooth manufacturers.

The conventional shade guide has an average of 12 shade selections fixedly mounted in sequence on a common holder. The dentist must match one of these shades to the existing teeth in the patient's mouth. If the patient is edentulous, then the dentist will select a shade according to the age of the patient based on his experience. When the selection is made, the doctor must write down the shade number (and/or brand of teeth or material) on a prescription. The prescription, plus the impression (usually made of silicone, alginate or rubber base) are sent to a laboratory where the appliance is fabricated. The laboratory set-up man or master technician will have to select the teeth (for dentures, partials or implant over dentures) or the tooth materials (for crowns, bridges, laminates or veneers) matching the shade number given by the doctor in the prescription.

Most of the time this procedure does not guarantee a perfect match because of many factors:

1. The shade guide in the hands of the doctor is not the same as the one in the hands of the lab.
2. The shade guide in the hands of the doctor was purchased many years previously while the shade guide and/or inventory of teeth and tooth materials, in the hands of the technician are of recent manufacture or different batches and different aging.
3. The doctor misread the color number on the shade guide or did not match the shade correctly.
4. The doctor's shade guide was overexposed to sunlight or it was constantly disinfected or sterilized modifying the original tones.
5. The technician is constructing an appliance without having a good idea of the patient's shade because he/she has not seen the patient. (The most sophisticated and experienced doctors send their patients to see their lab master technicians to verify the shades).
6. The manufacturer made a mistake and the shade in the guide is not identified correctly.
7. The manufacturer slightly changed the shades in its production batches of teeth or tooth powder because of forced changes of one ingredient.

In these cases, the dentist will send back the appliance because the shade does not match and this problem cannot be fixed at chairside. While most of the mechanical problems can be fixed at chairside, these recurring problems of shade matching can not and result in loss of labor time.

It is the prime object of the present invention to overcome the difficulties and disadvantages of the prior devices and to avoid additional loss of time, money and terrible inconvenience for the patient.

It is the object of this invention to provide a more precise method of selecting the shade of teeth and tooth material according to our actual physical reference.

Artificial teeth, and materials to custom make them, are manufactured by several companies and facilities throughout the world. The dentist is nevertheless capable of making the selection from any one of a number of these manufacturers and suppliers.

The foregoing objects, as well as others, will be apparent from the following disclosure of the present invention.

BRIEF SUMMARY OF THE INVENTION

According to the present invention, a device is provided with which the dentist can easily, safely and securely communicate with the laboratory technician who fabricates the dental applicance. The device comprises a housing with at least two tooth shade reference tabs, all three of which are identified with the same serial number. The dentist will stock several shade reference devices with different shades, each considered a shade unit. The dentist may first use the conventional regular shade guide FIG. 1 and then verify the shade picked with one of the shade reference units of the present invention in his inventory or kit. When the desired unit is selected, the dentist will then send one of the tooth shade tabs in the inventive unit to the lab, together with the more generical prescription and the impression. The laboratory will thus receive the physical shade tab reference which is the perfect match wanted by the dentist. It is then the responsibility of the laboratory to match the appliance shade or color to the shade reference supplied to him. The dentist will keep the housing and the remaining tooth shade tab of the reference unit in the patient's file. The date and the name of the patient will be written in the space provided on the back of the unit housing. When the appliance is supplied to the dentist, it will be easy and simple for him to compare it to the reference unit in his file.

Expressed in greater detail, the invention comprises a shade guide which comprises a plastic holder having a generally rectangular shape and a plurality of elongated slots. Each of the tabs and the plastic holder are provided with cooperating recesses and detents to hold the tabs in place and are provided with flat surfaces on one side on which personal identifying data can be placed. When in use, one of the guides is removed from the frame and sent to the technician for use in making the prosthesis for the patient. The other of the guides is retained by the dentist in the patient's file so as to be available when the prosthesis is returned.

Full details of the present invention are set forth in the following description of the preferred embodiments and illustrated in the accompanying drawing.

BRIEF DESCRIPTION OF THE DRAWINGS

In The Drawings:

FIG. 1 is an elevational view of a conventional prior art shade guide;

FIG. 2 is a front perspective view of the assembly of the shade guide tabs and holder;

FIG. 3 is a rear elevational view of the shade guide tabs;

FIG. 4 is a rear elevational view of the holder.

DESCRIPTION OF THE INVENTION

As seen in FIG. 2, the present invention provides a holder generally referred to by numeral 10 in which is held at least a pair of identical shade guide tabs, generally referred to by the numeral 12. As seen in FIG. 2, each of the shade guides 10 includes a flat, enlongated handle 14 and a sample tooth 16 or tooth portion supported at one end of the handle so that it may, as is customary, be held by the handle next to the patient's real teeth during the selection process. The manufacturer's code or identification number 18 is imprinted on the front of the handle and in this version, additional information or data 20 may be embossed or printed on the remainder of the front or the back of the handle. In accordance with the present invention, a small ridge detent 22 is provided on the back surface of the handle at the end opposite the tooth 16.

The holder 10 as seen in FIGS. 2 and 4, comrpises a frame-like member divided into three elongated slots 24. The slots 24 have a front to rear depth and side to side width providing slidable entry of the handle 14 of the shade guide 12 with very little play therein. The holder 10 comprises a base 26 from which extends a shallow lower rear wall 28 and a plurality of parallel, thin partitions forming a pair of outside side walls 30 and 32 and inner walls 34 defining the slots 24. A transverse strip 36 extends along the upper edge forming an upper back wall. In addition, the frame includes a front brace 38 extending transversely from the side wall 30 to side wall 32 intermediate the base and the upper rear wall. The brace 38 is set below the frontal edges of the side walls 30 and 32 so that the depth of the slots 24, from front to back, is reduced in opposition to the free area between the lower and upper back walls. In this manner, the shade guide handle 14 enters through the upper end of each of the slots 24 and is restricted by the front brace 38 which resiliently acts on the handle 14 to maintain a clamping pressure thereon, preventing the shade guide from falling out of or being easily removed from the slot once it is placed therein. The detent 22 on the rear surface of the handle 14, coacts with the lower rear wall 28 to increase the tension or compression on the handle holding it in place. The rear wall is formed with a transversely elongated slot 40 which is adapted to receive the detent 22 creating a sort of snap action once the shade guide is inserted into the frame.

While in the embodiment shown of the drawings there are three slots 24 for three shade guides 12, it will be appreciated that the holder can be made with two or four of these slots. Not all of the slots must be simultaneously used.

The rear surface of the lower rear wall 28 may be used to apply indicia as at 42 and information thereto as desired by the dentist and/or the manufacturer. Indicia may also be carried by the front brace 40.

Preferably, the system of the present invention is employed initially by the manufacturer who supplies his entire shade guide sample kit including the conventional guides to the dentist, with a complete set of the present shade guide units identically duplicate in a single holder, respectively. The dentist may then make his comparison, in the conventional manner, using one shade guide from the selected holders until the proper selection is made. Thereafter, the dentist removes one shade guide of the identical pair, sending it to the supplier or manufacturer for the exact replication of the artificial teeth, at least by color. At the same time, the dentist retains one of the selected pair for future reference. The manufacturer will, of course, replace the sample guides upon receipt of the order for the artificial teeth.

As will be seen from the foregoing, the system of the invention presents many advantages. For example, it permits the dentist to send a complete item to the laboratory with identifying data while retaining a like item in the holder, thus providing easy coordination between the dentist and the technician and the assurance that the material provided by the manufacturer is that which was ordered by the dentist or technician. In addition, the holder itself may be used in shipping the shade guide between dentist and technician since it will retain the shade guide and hold it against harm. The system is simple and it may be used repeatedly.

The present invention has a further advantage in that the holder, with the shade guide, may be easily retained in narrow elongated trays and may be arranged in consecutive color order for easy manipulation and selection. In this storage condition, the holder can be easily held upright so that the sample tooth will always be easily visible.

Various changes and modifications are apparent from the foregoing disclosure and others will suggest themselves to those skilled in the art. It is therefore to be understood that the following disclosure is illustrative only and not limiting of the invention.

What is claimed is:

1. A system for use by a dentist in selecting a tooth color for a patient for whom artificial teeth are to be made, said system comprising a holder and dual identical shade guides being identically shaded and removably supported in said holder, each of said dual shade guides including an elongated handle having a tooth sample supported on one end thereof and identical indicia, said shade guides being removable from said holder for one to be sent to the tooth manufacture for use as a guide in making teeth for said patient while the other of said shade guides may be retained by the dentist in said frame.

2. A system according to claim 1, wherein the holder also includes an area for recording the patient's personal identifying data.

3. A system for use by a dentist for selecting a tooth color for a patient for whom artificial teeth are to be made, said system comprising a plastic holder having a generally rectangular shape and a plurality of elongated slots, and dual identical shade guides being identically shaded and removably supported in said respective slots, each of said dual shade guides including a flat, elongated member, a tooth sample removably supported on one end thereof, said tooth identified by a central code and having a shade substantially the same as the teeth of said patient, and when in use, one of said shade guide being removed from said frame and sent to the laboratory for use as a guide in making teeth for said patient while the other of said shade guide is retained by the dentist in said frame.

4. A system according to claim 3, wherein the holder also includes a surface area for recording the patient's personal identifying data.

* * * * *